(12) United States Patent
Puterbaugh et al.

(10) Patent No.: US 10,591,006 B2
(45) Date of Patent: Mar. 17, 2020

(54) AUTOMATICALLY ACTUATED SPLIT-COLLAR ACTIVE MECHANICAL BRAKE FOR SURGICAL LIGHTING SYSTEMS

(71) Applicant: AMERICAN STERILIZER COMPANY, Mentor, OH (US)

(72) Inventors: Nicholas G. Puterbaugh, Mentor-on-the-Lake, OH (US); Christopher R Mohr, Mentor, OH (US)

(73) Assignee: American Sterilizer Company, Mentor, OH (US)

(*) Notice: Subject to any disclaimer, the term of this patent is extended or adjusted under 35 U.S.C. 154(b) by 133 days.

(21) Appl. No.: 15/809,117

(22) Filed: Nov. 10, 2017

(65) Prior Publication Data

US 2019/0145473 A1 May 16, 2019

(51) Int. Cl.
*A47H 1/10* (2006.01)
*F16D 65/12* (2006.01)
(Continued)

(52) U.S. Cl.
CPC .............. *F16D 65/12* (2013.01); *A61B 90/35* (2016.02); *A61B 90/50* (2016.02); *A61G 12/004* (2013.01);
(Continued)

(58) Field of Classification Search
CPC ...... F16M 13/027; F16M 11/08; F16D 65/12; A61B 90/35
USPC ............ 248/325, 424, 343, 344, 583, 278.1, 248/249.1; 362/371, 402, 804, 572, 220, 362/249.11
See application file for complete search history.

(56) References Cited

U.S. PATENT DOCUMENTS 2,317,481 A 4/1943 Peterson et al.
3,164,355 A 1/1965 Seitz et al.
(Continued)

FOREIGN PATENT DOCUMENTS

FR 1441338 7/1965

OTHER PUBLICATIONS

International Search Report Issued in corresponding International Patent Application No. PCT/US18/48776, dated Nov. 26, 2018.

*Primary Examiner* — Todd M Epps
(74) *Attorney, Agent, or Firm* — Kusner & Jaffe

(57) ABSTRACT

A brake assembly for braking relative rotational movement of a spindle that is moveable about a central axis relative to a hub. The brake assembly is comprised of a collar comprised of a pair of arcuate leg sections, having a first end pivotally linked together to allow pivoting movement of the leg sections. A frictional surface is provided along the inner surface of each of leg section. An adjustable fastening assembly connects second ends of the leg sections together and clamps the leg sections to the spindle with the frictional surface on the leg sections engaging the outer surface of the spindle. A stop member is connected to the hub and is disposed to engage a surface of the leg sections, wherein rotation of the spindle in a first direction about the axis causes a surface of one of the leg sections to engage the stop and to reduce frictional engagement of one of said leg sections by releasing engagement with the spindle as the spindle moves in said first direction.

9 Claims, 5 Drawing Sheets

(51) Int. Cl.
*A61B 90/35* (2016.01)
*A61B 90/50* (2016.01)
*F21V 21/26* (2006.01)
*F16M 11/08* (2006.01)
*A61G 12/00* (2006.01)
*F16M 13/02* (2006.01)
*F21W 131/205* (2006.01)
*F21V 33/00* (2006.01)

(52) U.S. Cl.
CPC .......... *F16M 11/08* (2013.01); *F16M 13/027* (2013.01); *F21V 21/26* (2013.01); *F21V 33/0068* (2013.01); *F21W 2131/205* (2013.01)

(56) References Cited

U.S. PATENT DOCUMENTS

| | | | |
|---|---|---|---|
| 3,936,671 A | 2/1976 | Bobrick et al. | |
| 4,200,407 A | 4/1980 | Bianco | |
| 4,345,847 A | 8/1982 | Schiff et al. | |
| 5,597,146 A | 1/1997 | Putman | |
| 5,730,410 A | 3/1998 | Archambault et al. | |
| 6,030,103 A | 2/2000 | Gampe et al. | |
| 6,793,380 B2 * | 9/2004 | Kupfer | A61B 90/35 362/371 |
| 6,817,585 B2 | 11/2004 | Wagner et al. | |
| 6,899,442 B2 * | 5/2005 | Howell | E04B 9/006 248/278.1 |
| D629,016 S | 12/2010 | Brooks et al. | |
| 8,070,331 B2 | 12/2011 | Gull et al. | |
| 8,888,696 B2 * | 11/2014 | Marka | A61B 90/35 600/249 |
| 2003/0189145 A1 | 10/2003 | Lindsay | |

* cited by examiner

AUTOMATICALLY ACTUATED SPLIT-COLLAR ACTIVE MECHANICAL BRAKE FOR SURGICAL LIGHTING SYSTEMS

FIELD OF INVENTION

The present invention relates to ceiling mounted systems for use in surgical theatres and more particularly to brake systems for articulating arms (booms) that support surgical lights, monitors, cameras, and the like, that are used during a surgical procedure.

BACKGROUND OF THE INVENTION

It is known to mount surgical lights, cameras and monitors that are used in a surgical suite to ceiling mounted structures that include a plurality of booms or arms that support the light fixtures, monitors and cameras. Each boom, or arm, is generally comprised of several sections that can pivot horizontally relative to each other or about vertical axes. The problem with such support systems is that once a light fixture, monitor or camera is positioned by a surgeon or hospital staff, it is necessary to have some kind of brake to maintain the position of the light fixture, monitor or camera. In this respect, it is extremely difficult to align the central support post or hub that is mounted to the ceiling in exactly a vertical orientation. Moreover, the weight of the medical equipment at the end of a support arm tends to distort the vertical alignment of the central hub, thereby causing drifting or shifting of the equipment, i.e., the lights, monitors or cameras, unless some kind of brake prevents such movement.

It is known to employ brake pads that are tightened and set by mechanical fasteners to maintain a position of the boom or arm once the position of the medical equipment at the end of the arm is set. However, it is necessary to overcome the mechanical friction created by these pads when moving the boom arms and medical equipment to a new position. Moreover, fastener-tighten brake pads wear over time, thus requiring constant adjustment or maintenance. Electromechanical brakes are also known, where a brake is released to allow movement of the arms and reset once a desired position is obtained. Electromechanical assemblies, however, are more complex and require activation and deactivation of the brake system.

The present invention provides a mechanical brake that releases itself when movement is initiated and reclamps upon a spindle when a desired position of the boom or arm has been reached and the moving force exerted on the boom or arm has been removed.

SUMMARY OF THE INVENTION

In accordance with the present invention, there is provided a brake assembly for braking relative rotational movement of a spindle that is moveable about a central axis relative to a hub. The brake assembly is comprised of a collar comprised of a pair of arcuate leg sections. Each of the leg sections has a first end and a second end. The leg sections are pivotally linked together at the first ends thereof to allow pivoting movement of the leg sections about the first ends thereof. A friction surface is defined along the inner surface of each of the leg sections. An adjustable fastening assembly connects the second ends of the leg sections together and clamps the leg sections to the spindle with the friction surface on the leg sections engaging the outer surface of the spindle. A stop member is connected to the hub. The stop is disposed to engage a surface of the leg sections, wherein rotation of the spindle in a first direction about the axis causes a surface of one of the leg sections to engage the stop and to reduce frictional engagement of one of the leg sections with the spindle as the spindle moves in the first direction, and wherein movement of the spindle in an opposite direction to the first direction causes the stop to engage a surface of another of the leg sections to cause the another of the leg sections to reduce friction engagement with the spindle.

In accordance with another aspect of the present invention, there is provided an adjustable friction apparatus for use on a support structure in a surgical theatre. The friction apparatus is comprised of a support having a spindle that is symmetrical about a central axis. A hub is moveable relative to the spindle. A split-collar ring disposed on the spindle has a frictional surface disposed along an inner surface of the ring for engaging an outer surface of the spindle. The ring has a gap that defines two leg portions. A cutout in the ring opposite to the gap allows the free ends of the leg portions to flex towards each other. A fastener extends through the free ends of the leg portions for releasably fastening the leg portions to the spindle. The fastener is operable to releasably bias the ends of the leg portions toward each other wherein the friction elements apply a clamping force to the spindle. A stop connected to the hub is disposed to engage the free ends of the leg portions, wherein rotation of said spindle in a first direction causes said clamp ring to engage said stop on a first surface on one of the leg portions, and forces the leg portions away from the spindle to partially release the ring from clamping engagement with the spindle.

In accordance with yet another aspect of the present invention, there is provided a support structure for use in a surgical theater. The support structure is comprised of a support having a cylindrical hub that is symmetrical about a central axis. An arm is movable relative to the hub. The arm is connected to a spindle that is symmetrical to and movable about the central axis. The spindle has a cylindrical outer surface. A split collar is disposed between the hub and the spindle. The collar has a frictional surface disposed along an inner surface thereof. The frictional surface engages the outer surface of the spindle. The collar has two leg portions with free ends that are able to move toward and away from each other. An adjustable fastening element extends through the free ends of said leg portions. The fastening element is operable to clamp the collar onto the spindle, and to compress the frictional surface on the collar against said outer surface of the spindle. The fastening element includes biasing means for biasing the free ends of the leg portions toward each other. A mechanical stop is attached to the hub and disposed between the surface of the leg sections of the collar. The stop is operable to engage one of the surfaces on one of the leg sections when the spindle moves relative to the hub in a first direction about the axis and engages another surface of the other leg section when the spindle moves in a second direction about the axis, wherein the stop, when engaging a leg section, causes the leg section to reduce the frictional engagement between said leg section and the spindle.

An advantage of the present invention is a brake assembly for use on a surgical support system that is adjustable by varying the frictional force exerted between moving parts of a boom arm.

Another advantage of the present invention is a brake system as described above that releases or reduces a frictional force on the moving parts when the boom is being moved to a new position and resets a braking condition once movement of the boom has stopped.

Another advantage of the present invention is a brake system as described above, wherein the initial braking force can be adjusted.

A still further advantage of the present invention is a brake system as described above, that is easily adjusted and/or repaired.

Still further advantages of the invention will become apparent to those of ordinary skill in the art upon a reading and understanding of the following detailed description of the preferred embodiments.

BRIEF DESCRIPTION OF THE DRAWINGS

The invention may take form in various components and arrangement of components, and in various steps and arrangement of steps. The drawings are only for purposes of illustrating a preferred embodiment and are not for the purpose of limiting the same.

DETAILED DESCRIPTION OF THE PREFERRED EMBODIMENTS

Figure 1:
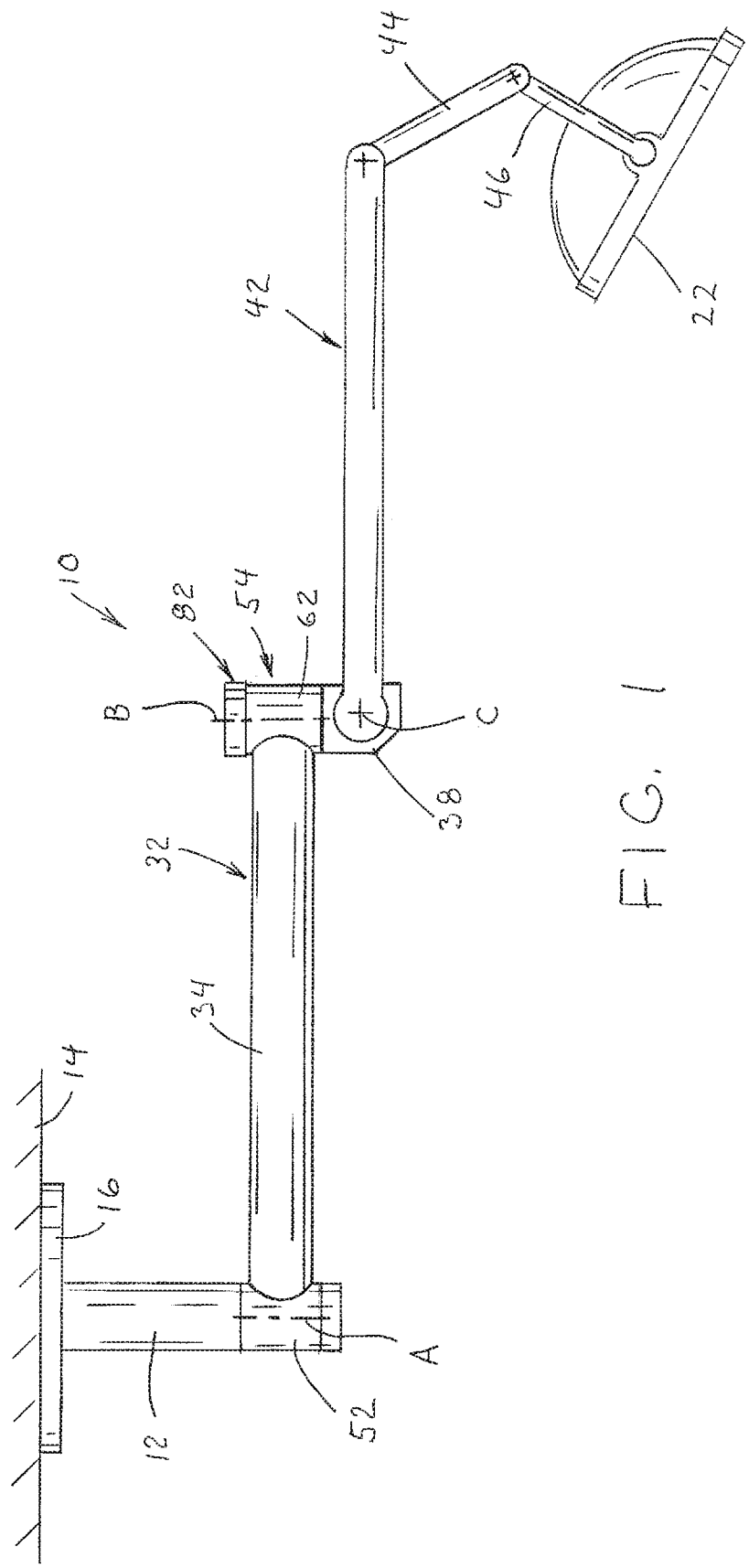
FIG. 1 is a side elevational view of a ceiling mounted surgical light assembly having a proximal boom arm section pivotally mounted to a central hub and a distal arm section pivotally mounted to the end of the proximal arm section.

Referring now to the drawings wherein the showing is for the purpose of illustrating a preferred embodiment of the invention only, and not for the purpose of limiting the same, FIG. 1 shows an arm assembly 10 for supporting a surgical light fixture 22 in a surgical suite. Although a light fixture 22 is shown, the support assembly 10 may be used to support a monitor or a video camera or some other medical device (not shown).

Arm assembly 10 is mounted by a central support 12 to a support member such as a ceiling 14 or wall mounted plate 16. Arm assembly 10 is provided to allow light fixture 22 to be positioned for achieving a desired level of illumination on a subject below. In this respect, arm assembly 10 is articulated to allow equipment, i.e., light fixture 22, to be positioned. In the embodiment shown, arm assembly 10 includes a proximal arm section 32 and a distal arm section 42.

In the embodiment shown, arm assembly 10 has two joints designated 52, 54. Joint 52 allows rotational movement of proximal arm 32 about a vertical axis "A" through central support 12, and joint 54 allows rotational movement of distal arm section 42 about a vertical axis "B" relative to proximal arm section 32. Proximal arm section 32 is comprised of an elongated member 34 that is connected at one end to joint 52 and at the other end to joint 54. A housing section 38 is connected to joint 54 and in turn is connected to distal arm section 42. Housing section 38 is connected to joint 54 to allow rotational movement of housing section 38 relative to joint 54 about vertical axis "B." Distal arm section 42 is connected to housing section 38 to allow pivotal movement of distal arm section 42 relative to housing section 38 about a horizontal axis "C." In the embodiment shown, the free end of distal arm section 42 is pivotally connected to an extension arm 44 that in turn is connected to a bracket 46 that is attached to light fixture 22.

Both joint assemblies 52, 54 allow pivotal movement of a spindle relative to a hub, as shall be described in greater detail below. Both are similar in design and function and therefore only one joint, namely, joint 54, shall be described in detail. As will be appreciated by those skilled in the art, the configuration of joint 54 is similar to joint 52. In the embodiment shown, joint 54 is merely an inverted version of joint 52.

Figure 2:
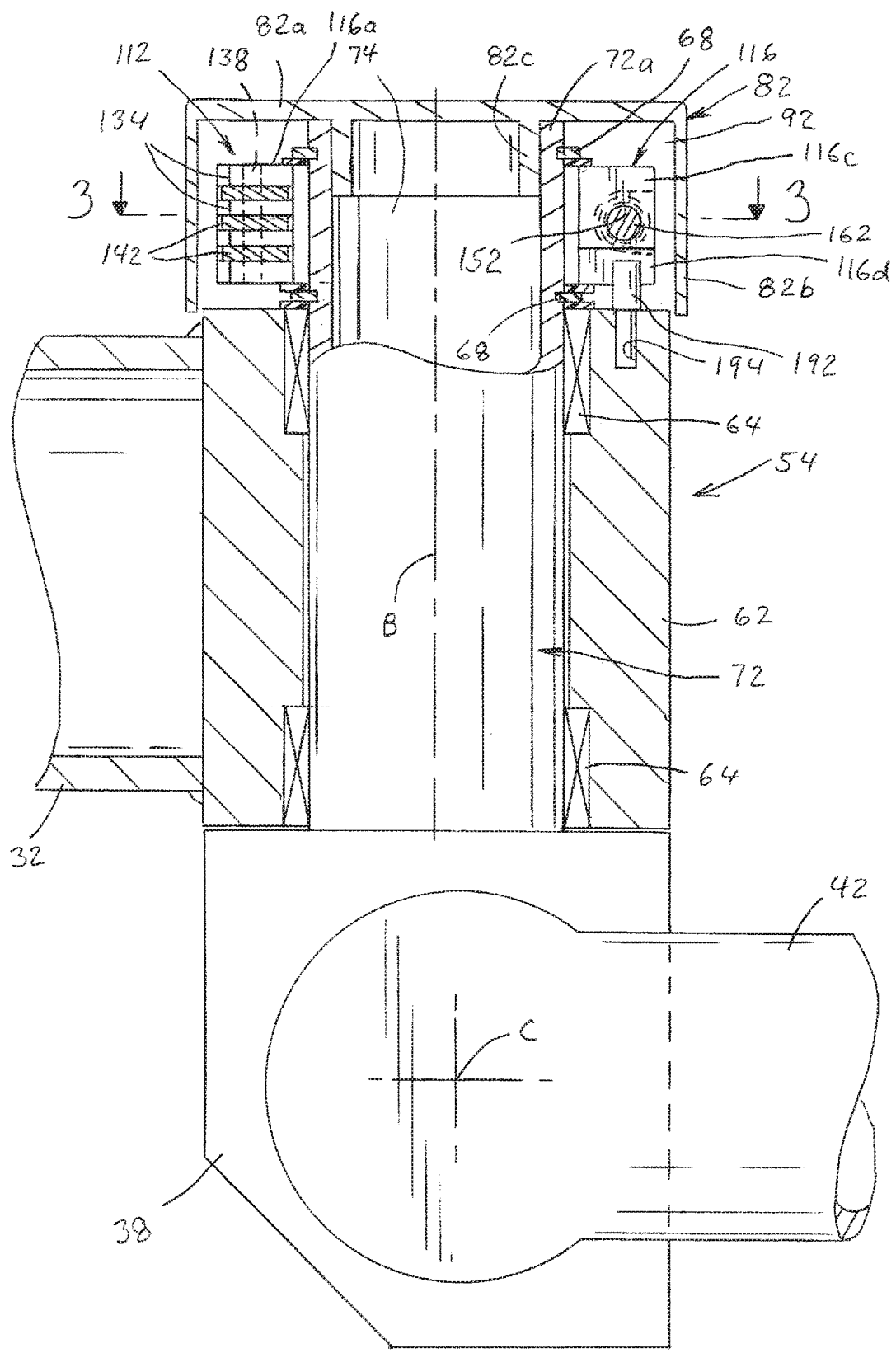
FIG. 2 is an enlarged sectional view of a pivoting joint between the proximal arm section and the distal arm section.
Figure 3:
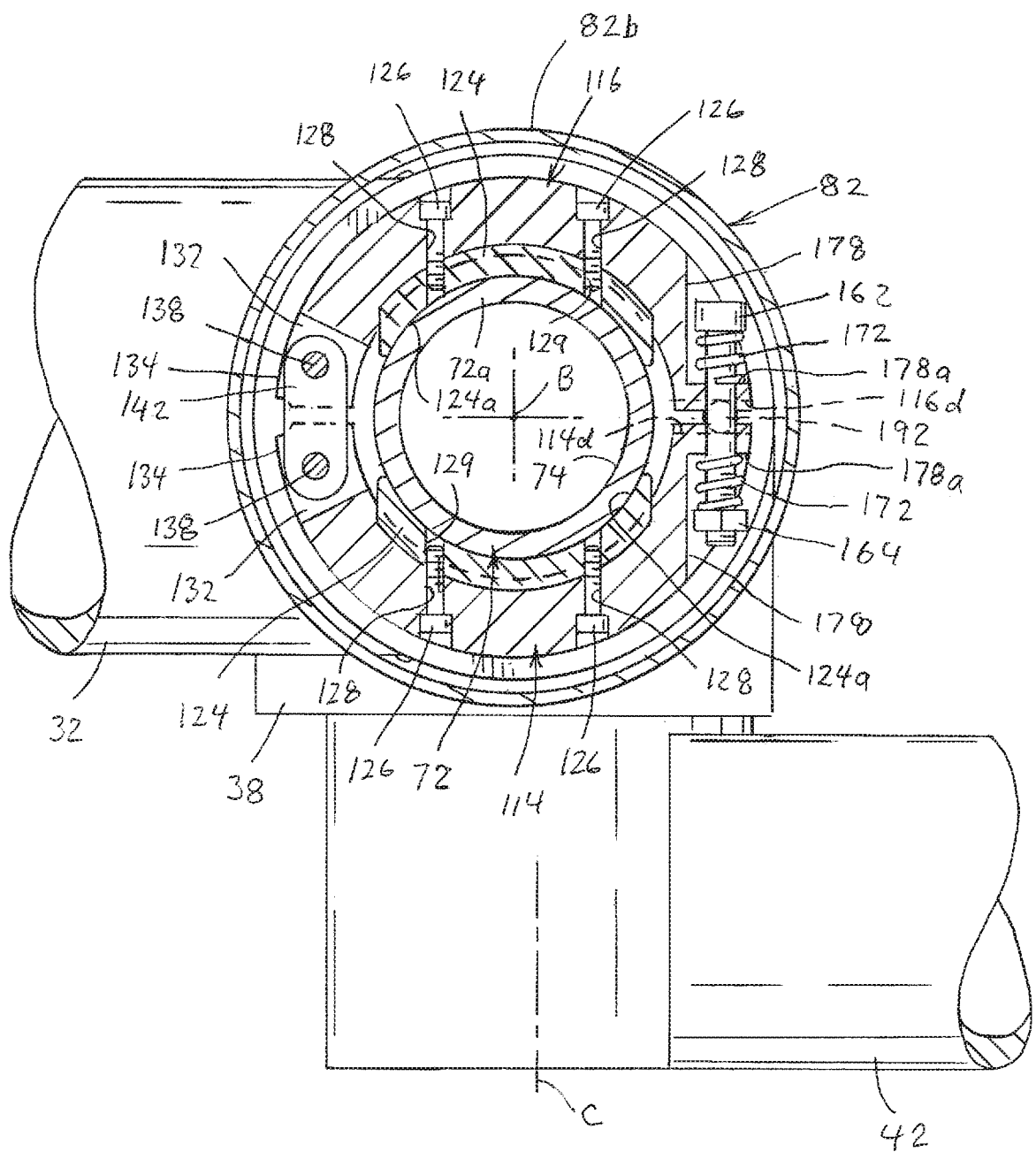
FIG. 3 is a sectional view taken along lines 3-3 of FIG. 2.
Figure 4:
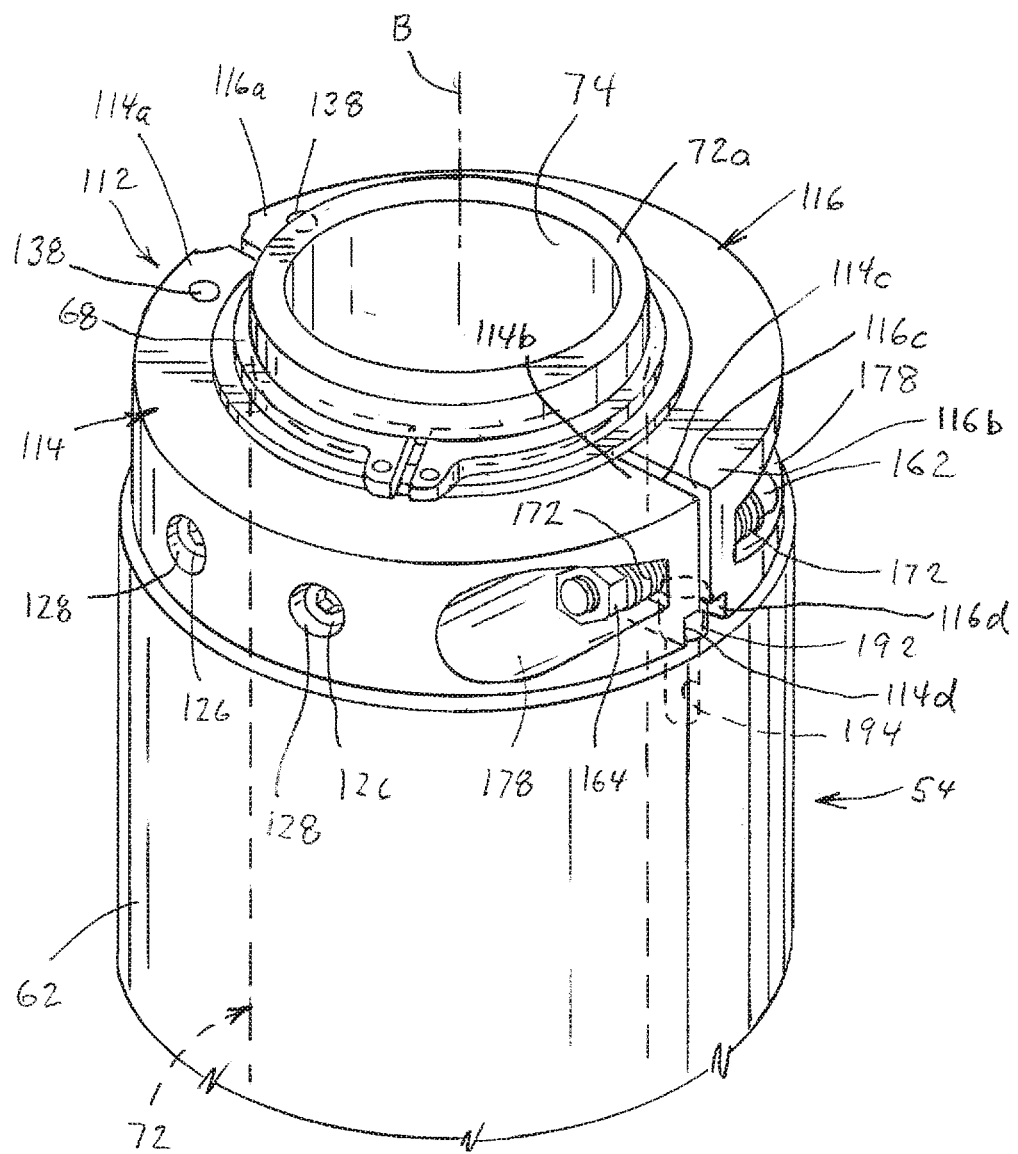
FIG. 4 is a perspective view of a mechanical brake assembly for controlling movement of the distal arm section relative to the proximal arm section.

Referring now to FIGS. 2 and 3, joint assembly 54 is best seen. Joint assembly 54 is comprised of a hub 62 that is connected to one end of proximal arm section 32 and a spindle 72 that is connected to housing section 38. Spindle 72 is disposed within hub 62 and is spaced therefrom by spaced-apart bearings 64. Spindle 72 and hub 62 are axially aligned along axis "B" in the drawings. A retaining ring 68, disposed within an annular slot in spindle 72, positions spindle 72 within hub 62.

As is best seen in FIG. 2, spindle 72 is longer in axial length than hub 62, wherein a portion 72a of spindle 72 extends beyond the upper end of hub 62. Spindle 72 is a cylindrical, tubular member that defines an elongated inner cavity 74. A cap 82 is provided at the upper end of spindle 72. Cap 82 is cap-shaped and includes an end wall 82a and a cylindrical outer wall 82b. Outer wall 82b is dimensioned to have an outer diameter generally matching the outer diameter of hub 62. Cap 82 also includes a cylindrical inner wall 82c disposed within outer wall 82b and spaced apart therefrom. Inner wall 82c has an outer diameter dimensioned to be received within cylindrical cavity 74 defined by spindle 72. Inner wall 82c is dimensioned to snugly fit within cavity 74. Outer wall 82b has an axial length to generally mate with the end of hub 62, as best seen in FIG. 2. Cap 82 defines an annular cavity 92 around spindle portion 72a at the end of hub 62.

Figure 5:
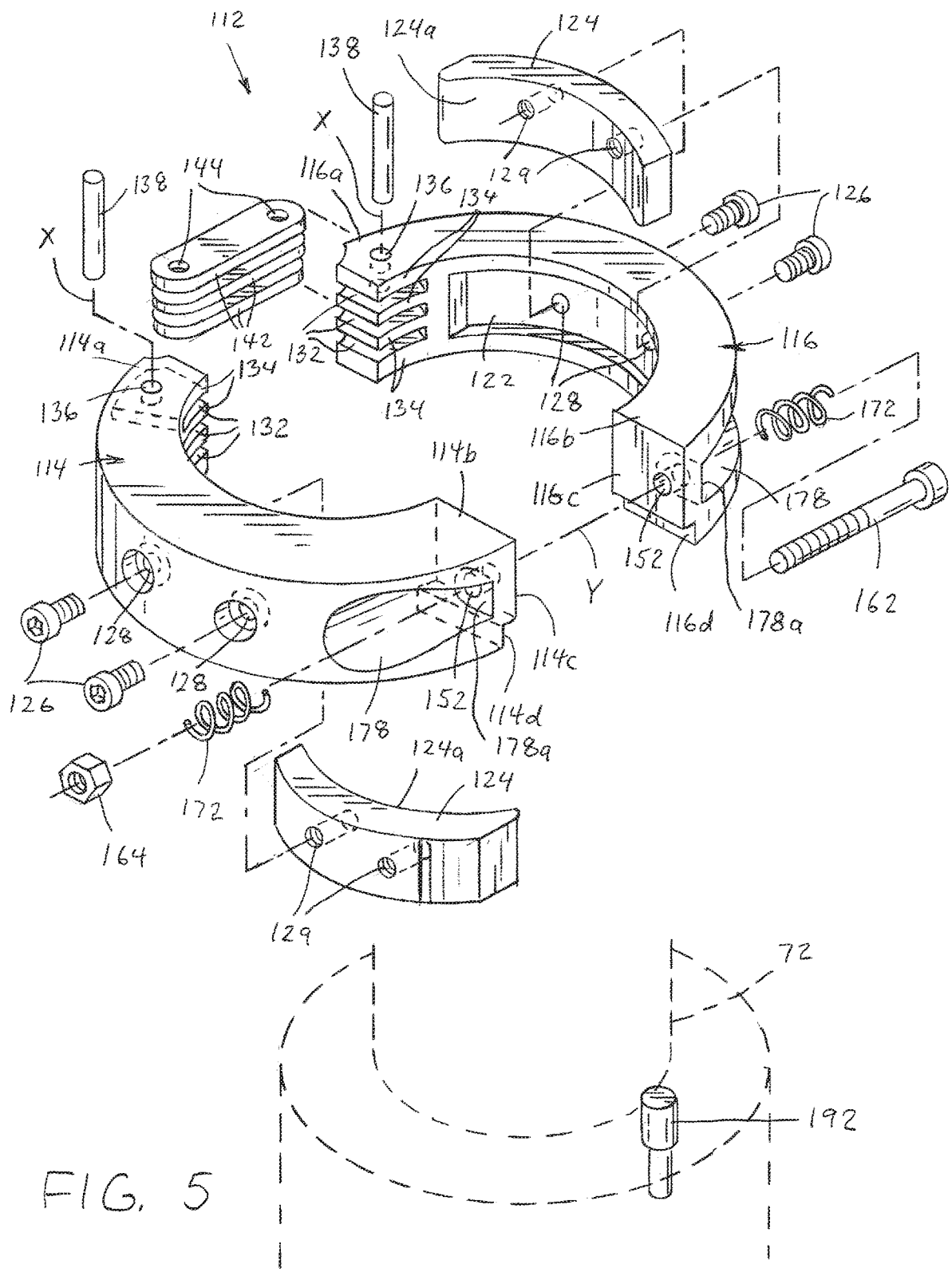
FIG. 5 is an exploded view of the brake assembly shown in FIG. 4.

In accordance with one aspect of the present invention, a brake assembly 112 is provided to retard relative movement between spindle 72 and hub 62. Brake assembly 112, best seen in FIG. 5, is basically an annular collar comprised of a first leg section 114 and a second leg section 116. In the embodiment shown, each leg section 114, 116 is arcuate in shape and is dimensioned to be clamped around spindle 72. An arcuate recess or groove 122 is formed in each leg section 114, 116 along the inner surfaces thereof to receive a friction element 124 having an inner friction surface 124a dimensioned to engage the outer surface of spindle 72.

Fasteners 126 extend through each leg section 114, 116 from an outer surface thereof to recess 122 defined along the inner surfaces of leg sections 114, 116. Fasteners 126 extend through openings 128 in leg sections 114, 116 and are received in mating threaded openings 129 in friction pad elements 124. Fasteners 126 are dimensioned to secure a friction element 124 to each leg section 114, 116. Each leg section 114, 116 has a first end 114a, 116a and a second end 114b, 116b. First ends 114a, 116a of leg sections 114, 116 are connected together such that second ends 114b, 116b of leg sections 114, 116 are pivotally moveable about first ends 114a, 116a of leg sections 114, 116. A plurality of parallel slots 132 is formed in first ends 114a, 116a of leg sections 114, 116. Slots 132 are spaced apart and dimensioned to be perpendicular to a central axis. Slots 132 define a plurality of parallel, spaced-apart finger-like plates 134. An aligned, cylindrical opening 136 is found along an axis "X" that extends through plates 134 at first ends 114a, 116a of leg sections 114, 116. Openings 136 are dimensioned to receive an elongated cylindrical pin 138. In the embodiment shown, each leg section 114, 116 includes four finger-like plates 134 extending from first ends 114*a*, 116*a* of leg sections 114, 116. A plurality of links 142 is dimensioned to connect first ends 114*a*, 116*a* of leg sections 114, 116 to each other. In the embodiment shown, each link 142 is an obround plate having a cylindrical opening 144 at each end thereof. Pin 138, that extends through openings 136 in plates 134 on first ends 114*a*, 116*a* of leg sections 114, 116, also extends through openings 144 in links 142. Pin 138 allows pivotal movement of leg sections 114, 116 relative to links 142.

Each leg section 114, 116 has an end face 114*c*, 116*c* at second end 114*b*, 116*b* thereof. When connected to links 142, end faces 114*c*, 116*c* of leg portions 114, 116 oppose each other, as shown in the drawings. End faces 114*c*, 116*c* are notched to defined recessed end faces 114*d*, 116*d* that are spaced from end face 114*c*, 116*c*. Cylindrical openings 152 are formed in second end 114*b*, 116*b* of leg sections 114, 116. Openings 152 extend through end faces 114*c*, 116*c* in the leg sections and are aligned along an axis "Y" that lies in a plane perpendicular to axis "X" through first end 114*a*, 116*a* of leg sections 114, 116. An elongated fastener 162 extends through openings 152 in second ends 114*b*, 116*b* of leg sections 114, 116. In the embodiment shown, fastener 162 is an elongated conventional cap screw that is dimensioned to extend through openings 152 in second ends 114*b*, 116*b* of leg sections 114, 116. A conventional threaded nut 164 is dimensioned to attach to the threaded end of fastener 162. Biasing means in the form of helical springs 172 are disposed on fastener 162. A spring 172 is disposed between the cap head of fastener 162 and the outer surface of second leg section 116 and spring 172 is provided on the end of fastener 162 between nut 164 and the outer surface of first leg section 114. In this respect, fastener 162 and nut 164 attach second ends 114*b*, 116*b* of leg sections 114, 116 to each other in a manner that allows movement of second ends 114*b*, 116*b* away from each other against the biasing force of springs 172 on fastener 162. In other words, second ends 114*b*, 116*b* of leg sections 114, 116 are secured together, but they are free to move against a biasing force away from each other.

The outer surfaces of leg sections 114, 116 are counter bored along axis "Y" to define cylindrical cavities 178 in second ends 114*b*, 116*b* of leg sections 114, 116. Cavities 178 are dimensioned to receive fastener 162 and spring 172, as best seen in FIG. 3. Cavities 178 define end surfaces 178*a* against which springs 172 abut.

When leg sections 114, 116 are attached together, brake assembly 112 essentially defines an annular ring or collar that is dimensioned to fit around spindle 72. Brake assembly 112 is dimensioned to be attached to spindle 72 at a location adjacent one end of hub 62, as best seen in FIG. 2. A pin or stop 192 is disposed in an opening or gap defined between recessed end surfaces 114*d*, 116*d* of leg sections 114, 116. As will be described in greater detail below, stop 192 is adapted to engage recessed end surfaces 114*d*, 116*d* on the free end of leg portions 114, 116. In the embodiment shown, stop 192 is in the form of a cylindrical pin having one end that is dimensioned to be received within a cylindrical opening 194 within the end face of hub 62. In this respect, in the embodiment shown, stop 192 extends along an axis generally parallel to central axis "B" of spindle 72 and hub 62 and is disposed in a position to engage a surface on leg sections 114, 116.

Braking assembly 112 is mounted to spindle 72 between two spaced-apart lock rings 68 that are received in annular grooves in spindle 72, as best seen in FIG. 2.

As illustrated in FIG. 2, when mounted to spindle 72, stop 192 is disposed in the opening defined between recessed end faces 114*d* and 116*d*, and friction elements 124 engages the outer surface of spindle 72, as best seen in FIG. 3.

Referring now to the operation to brake assembly 112, when mounted on to spindle 72, frictional elements 124 on leg sections 114, 116 frictionally engage the outer surface of spindle 72. In this respect, rotation of spindle 72 relative to hub 62 only occurs when sufficient force is applied to distal arm section 42 to overcome the frictional force exerted by brake assembly 112. In this respect, the amount of frictional force applied by frictional elements 124 can be adjusted by tightening or releasing fastener 162, which in turn increases or decreases the clamping force applied onto frictional elements 124 against the outer surface of spindle 72.

In accordance with one aspect of the present invention, rotation of spindle 72 relative to hub 62 occurs when sufficient rotational force is applied to overcome the frictional force exerted by the brake assembly onto spindle 72. Depending upon the direction of the rotation, once the relative rotational force applied to distal arm 42 exceeds the frictional force applied by the brake assembly onto spindle 72 rotation of the hub 62 relative to spindle 72 can occur. Rotation of spindle 72 relative to hub 62 causes stop 192 to engage either recessed end surface 114*d* or recessed end surface 116*d*, depending on the direction of rotation, as indicated above. Further rotation of spindle 72 relative to hub 62 occurs when sufficient rotational force is applied to overcome the braking force exerted on the spindle by brake assembly 112. If the rotational force is constant, engagement between stop 192 and one of leg sections 114, 116 causes the engaged leg section to be pushed away from engagement with spindle 72 as the rotational force continues. In other words, one of the leg sections pivots away slightly from engagement with the spindle to allow easier relative rotation of spindle 72 relative to hub 62 as compared to a situation where both frictional elements 124 maintain engagement with spindle 72. Once a desired position for distal arm section 42 has been achieved and the moving force exerted on distal arm 42 is removed, further force exerted by pin 192 against a recessed surface of one of the arm sections terminates, and the brake assembly 112 again clamps onto spindle 72 to prevent further rotational movement or drifting of spindle 72 relative to hub 62.

In other words, brake assembly 112 allows a user of arm assembly 10 to move proximal arm 32 and distal arm 42 relative to each other by applying sufficient rotational force on spindle 72 relative to hub 62 to overcome the original clamping pressure exerted by fastener 62 and brake assembly 112 on spindle 72. So long as the rotational force is applied, pin 192 will move one or the other leg sections 114, 116 slightly away from engagement with spindle 72 to reduce the frictional force applied to spindle 72 and to allow continued rotational movement of spindle 72 relative to hub 62. In this respect, leg sections 114, 116 move against the biasing force of springs 172 to allow slightly freer movement of spindle 72 relative to hub section 62. Once the moving force applied between the spindle 72 and hub 62 is removed, springs 172 on fastener 162 clamp brake assembly back into its original position on spindle 72, thereby preventing drifting of distal arm 42 relative to proximal arm 32. In other words, rotation of spindle 72 in a first direction about axis B causes a surface of one of leg sections 114, 116 to engage stop 192 and thereby reduce frictional engagement of the one leg section with spindle 72 as the spindle moves in a first direction.

Movement of spindle 72 in an opposite direction to the first direction causes stop 192 to engage a surface of the other leg section so as to cause the other leg section to reduce frictional engagement with spindle 72.

The present invention thus provides a mechanical brake assembly that releases itself when movement is initiated and reclamps onto a spindle when a desired position of an arm section has been reached. The present invention further provides a brake assembly wherein the initial braking force applied by brake assembly 112 onto spindle 72 can be adjusted.

The present invention has been described with respect to a preferred embodiment of the invention only. Other embodiments will occur to those skilled in the art from a reading of the foregoing description. For example, in the embodiment shown, stop 192 is shown mounted onto hub 62. As will be appreciated, surfaces can be provided on leg sections 114, 116 to engage surfaces on hub 62 to release an arm section depending on the direction of the rotation. These and other advantages will be apparent to those skilled in the art upon the reading of the present disclosure. It is intended that all such modifications be included.

Having described the invention, the following is claimed:

1. A brake assembly for braking relative rotational movement of a spindle that is moveable about a central axis relative to a hub, said brake assembly comprised of:
    a collar comprised of a pair of arcuate leg sections, each of said leg sections having a first end and a second end, said leg sections pivotally linked together at the first ends thereof to allow pivoting movement of said leg sections about the first ends thereof;
    a friction surface defined along an inner surface of each of said leg sections;
    an adjustable fastening assembly that connects said second ends of said leg sections together and clamps said leg sections to said spindle with said friction surface on said leg sections to engage an outer surface of said spindle; and,
    a surface on said hub disposed to engage a surface on one of said leg sections when said hub rotates in a first direction relative to said spindle, engagement of said surface on said one of said leg sections with said surface on said hub causes said leg section to reduce engagement between said leg section and said spindle.

2. A brake assembly according to claim 1, wherein said surface on said hub is a stop member connected to said hub, said stop member disposed to engage said surface on said one of said leg sections,
    wherein rotation of said spindle relative to said hub in a first direction about said axis causes said surface of said one of said leg sections to engage said stop and to reduce frictional engagement of one of said leg sections with said spindle as said spindle moves relative to said hub in said first direction.

3. A brake assembly according to claim 2, wherein movement of said spindle about said axis relative to said hub in an opposite direction to said first direction causes said stop to engage a surface of another of said leg sections to cause said another of said leg sections to reduce frictional engagement of said another leg section with said spindle.

4. A brake assembly according to claim 1, wherein said adjustable fastening assembly is comprised of an adjustable fastener extending through said second ends of said leg sections.

5. A brake assembly according to claim 4, further comprising bias elements on said fastener biasing said second ends of said leg sections toward each other, wherein said second ends of said leg sections can move away from each other when said surface on said hub engages a surface on a leg section.

6. An adjustable friction apparatus for use on a support structure in a surgical theatre, said friction apparatus comprising:
    a support having spindle that is symmetrical about a central axis;
    a hub moveable relative to said spindle;
    a split-collar ring disposed on said spindle having a frictional surface disposed along an inner surface of said ring for engaging an outer surface of said spindle, said ring having a gap that defines two leg sections;
    a cutout in said ring opposite to said gap that allows free ends of said leg sections to flex towards each other, said free ends of the leg sections being spaced apart from each other;
    a fastener extending through said free ends of the leg sections for releasably fastening said leg sections to said spindle, said fastener operable to releasably bias said free ends of said leg sections toward each other wherein said frictional surface applies a clamping force to said spindle; and,
    a surface on said hub disposed to engage a surface on one of said leg sections when said hub rotates in a first direction relative to said spindle, engagement of said surface on said one of said leg sections with said surface on said hub to cause said leg section to reduce engagement between said leg section and said spindle.

7. A support structure for use in a surgical theater, said support structure comprising:
    a support having a cylindrical hub that is symmetrical about a central axis;
    an arm movable relative to said hub, said arm connected to a spindle that is symmetrical to and movable about said central axis, said spindle having a cylindrical outer surface;
    a split collar disposed between said hub and said spindle, said collar having a frictional surface disposed along an inner surface thereof, said frictional surface engages the outer surface of said spindle;
    said collar having two leg sections with free ends that are able to move toward and away from each other;
    an adjustable fastening element extending through said free ends of said leg sections, said fastening element operable to clamp said collar onto said spindle, and to compress said frictional surface on said collar against said outer surface of said spindle, said fastening element including biasing means for biasing said free ends of said leg sections toward each other; and
    a surface on said hub disposed to engage a surface on one of said leg sections when said hub rotates in a first direction relative to said spindle, engagement of said surface on said one of said leg sections with said surface on said hub causes said leg section to reduce engagement between said leg section and said spindle.

8. A support structure for use in a surgical theater according to claim 7, wherein said surface on said hub is a mechanical stop attached to said hub and disposed between said leg sections of said collar, said stop operable to engage one of said leg sections when said spindle moves relative to said hub in a first direction about said axis and engage another of said leg sections when said spindle moves in a second direction about said axis, wherein said stop, when in engagement with a leg section, causes said leg section to reduce the frictional engagement between said leg section and said spindle.

9. A support structure for use in a surgical theater, said support structure comprising:
- a support having a cylindrical hub that is symmetrical about a central axis;
- an arm movable relative to said hub, said arm connected to a spindle that is symmetrical to and movable about said central axis, said spindle having a cylindrical outer surface;
- a split collar disposed between said hub and said spindle, said collar having a frictional surface disposed along an inner surface thereof, said frictional surface in engagement with the outer surface of said spindle;
- said collar having two leg sections with free ends that are able to move toward and away from each other;
- an adjustable fastening element extending through said free ends of said leg sections, said fastening element operable to clamp said collar onto said spindle, and to compress said frictional surface on said collar against said outer surface of said spindle, said fastening element including biasing means for biasing said free ends of said leg sections toward each other; and
- a surface on said hub disposed to engage a surface on one of said leg sections when said hub rotates in a first direction relative to said spindle, engagement of said surface on said one of said leg sections with said surface on said hub causes said leg section to reduce engagement between said leg section and said spindle.

* * * * *